(12) United States Patent
Wey

(10) Patent No.: US 6,293,963 B1
(45) Date of Patent: Sep. 25, 2001

(54) WATER ENERGIZING DEVICE FOR SHOWER BATH

(76) Inventor: Albert C. Wey, 233 E. 57 th St., Westmont, IL (US) 60559

( * ) Notice: Subject to any disclaimer, the term of this patent is extended or adjusted under 35 U.S.C. 154(b) by 0 days.

(21) Appl. No.: 09/487,641

(22) Filed: Jan. 19, 2000

(51) Int. Cl.$^7$ .................................................. A61H 33/00
(52) U.S. Cl. .............................. 607/81; 607/80; 607/82; 4/524; D24/203; D24/204; D24/209
(58) Field of Search .................. 607/80, 82; D24/203, D24/204, 209, 210; 4/615, 524, 525

(56) References Cited

U.S. PATENT DOCUMENTS

| | | | |
|---|---|---|---|
| D. 442,695 | * | 5/2001 | Charlier et al. ..................... D24/203 |
| 3,945,058 | * | 3/1976 | Gardner .................................... 4/163 |
| 4,300,556 | * | 11/1981 | Ochi et al. ............................ 128/256 |
| 4,945,908 | * | 8/1990 | Schneider .............................. 128/369 |
| 5,117,481 | * | 5/1992 | Sung ..................................... 392/416 |
| 5,255,399 | * | 10/1993 | Park ....................................... 4/525 |
| 5,741,317 | * | 4/1998 | Ostrow ................................... 607/85 |
| 5,792,184 | * | 8/1998 | Zhou et al. ............................... 607/1 |

* cited by examiner

Primary Examiner—Linda C. M. Dvorak
Assistant Examiner—A. Farah
(74) Attorney, Agent, or Firm—Piper Marbury Rudnick & Wolfe

(57) ABSTRACT

A water energizing device for shower bath comprising a far infrared rays emitting material that provides a means for enhancing the health conditions of human beings through a medium of water running through the far infrared irradiation zone formed by the device. The results are improved skin and hair condition, recovery from stress and fatigue, and enhanced blood circulation and metabolism of human body.

5 Claims, 1 Drawing Sheet

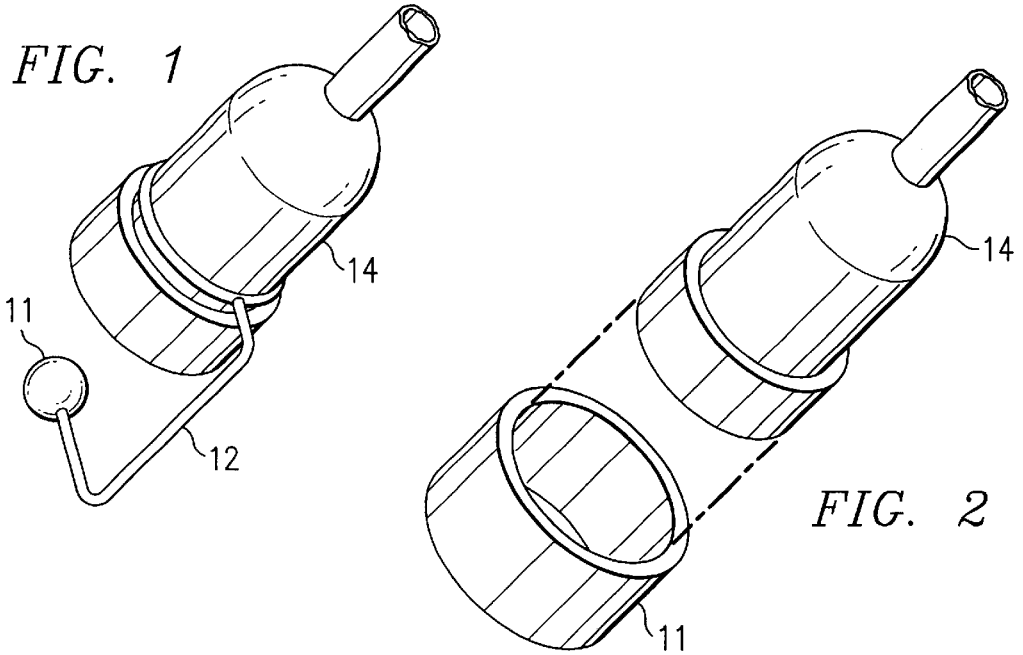
FIG. 1
FIG. 2
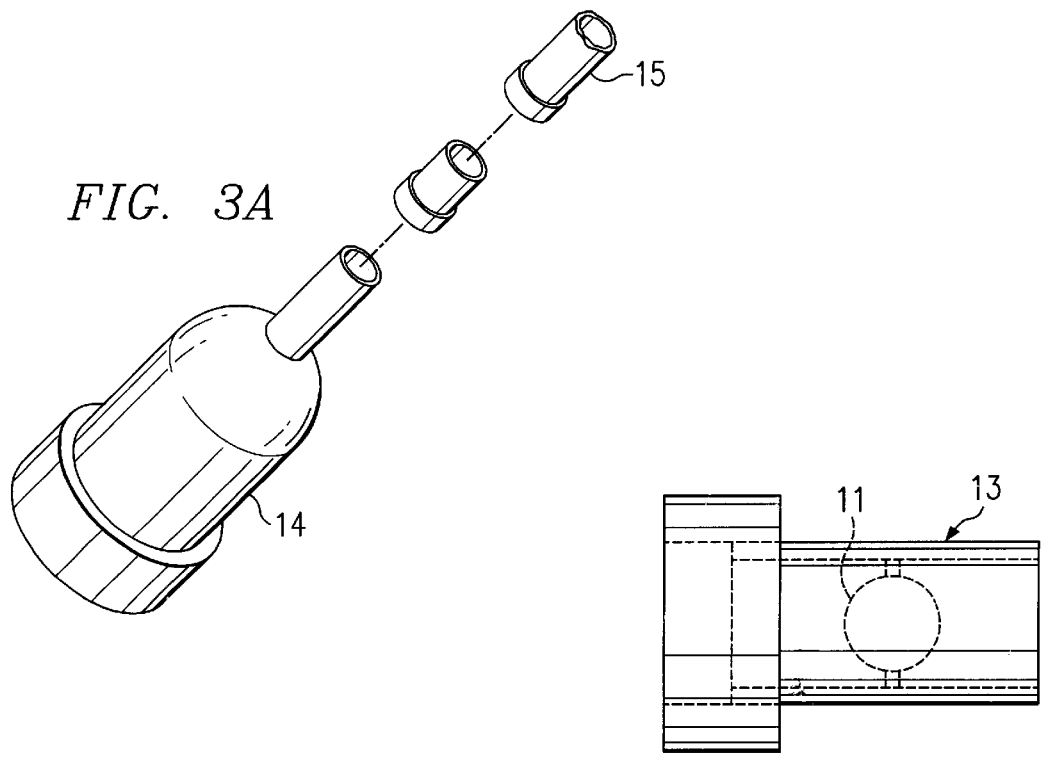
FIG. 3A
FIG. 3B

WATER ENERGIZING DEVICE FOR SHOWER BATH

BACKGROUND—FIELD OF INVENTION

This invention relates to a water energizing device for shower bath comprising a far infrared rays emitting material that can transport the photon energies of the far infrared emission to human body via a medium of water running through the far-infrared irradiation zone formed by the said far-infrared rays emitting material to enhance circulation and metabolism of the body and help recover from stress and fatigue.

BACKGROUND—DESCRIPTION OF PRIOR ART

There have been several types of far-infrared-emission related therapeutic devices developed for improving and maintaining health of human body. For example, one type of devices included a magnetic radiating unit on a far infrared ray generating composition plate (U.S. Pat. Nos. 5,451,199 and 5,894,067), the other devices comprised both germanium powder and ceramic powder for skin contact medical treatment (U.S. Pat. No. 4,976,706). These devices require skin contact with human body. Other devices employ far infrared emitting material to treat water in order to either improve the taste of the water or enhance the health of human body by drinking the treated water (U.S. Pat. Nos. 5,643,489 and 5,965,007). Far-infrared bathing units were developed, however, with complicated structure (U.S. Pat. Nos. 5,255,399 and 5,117,481). None of the prior arts teaches the use of a far-infrared rays emitting material attached to a showerhead to energize the water for shower bath.

It is known that far infrared radiation in a wavelength band of 3 $\mu$m to 14 $\mu$m has a strong resonance effect to substance having hydrogen bonding. According to Organic Chemistry, there exist dipole-dipole interactions between polarized molecules and hydrogen bonding is a strong form of such interactions. The electric potentials of such dipole-dipole interactions are in the range of 0.04 eV to 0.5 eV. Based on a simplified equation that governs the relationship between electric potential (eV) and the photon energy E associated with a wavelength $\lambda(\mu m)$: $\lambda(\mu m) = 1.2398$ (eV–$\mu$m)/E(eV), such dipole-dipole interactions will resonate with the electromagnetic waves having wavelengths between 2.5 $\mu$m to 30 $\mu$m, which fall in the far infrared radiation zone.

For example, Water molecule consists of two hydrogen (H) atoms and one oxygen (O) atom. The angle between the two oxygen-hydrogen chemical bonding (O—H) in water molecule is 104° so that the water molecules are polarized in nature. It means that the hydrogen atoms and oxygen atoms in water molecules are charged and tend to create a static hydrogen-bonding between water molecules. As a result, the charged water molecules gather and form large clusters. The hydrogen-bonding between water molecules has an electric potential about 0.35 eV and can be resonantly broken with a far infrared radiation at about 3.54 $\mu$m wavelength into individual molecules or smaller molecule clusters with better mobility. In addition, a 6.27 $\mu$m far infrared radiation can activate the water molecules by transferring photon energies of the radiation into symmetrical rotation of atoms in water molecules.

Therefore, water is a good absorbent of far-infrared radiation at the wavelengths 3.54 um and 6.27 um. The photon energies of far-infrared radiation are absorbed by clustered water molecules and used to break apart the clusters. The forced-apart water molecules, or smaller clusters, remain polarized (or called "energized") after absorbing the photons. Meanwhile, the energized water molecules tend to stabilize by regaining cluster formation with others. When it happens, photons with the same characteristics, namely the same wavelengths and photon energies, are released based on the Principle of Conservation of Momentum. The newly released photons can be recycled in breaking apart other clusters until they fully dissipate as heat or escape from the system. This makes water a great medium for "transporting" photon energy of far-infrared radiation and sets a platform for the development of the present invention.

In summary, the far-infrared radiation may not reach far in the air as its strength decays rapidly, adversely proportional to the square of distance. Nonetheless, it can use water as a medium to transport its energy. The photon energy can be tentatively stored in the medium and transported to the human body while the "energized" water is in close contact with the body as in the case of shower bath.

The photon energies absorbed by the skin can farther permeate 4 to 5 cm into human body and energize the water molecules and cells within. The "energized" water molecules and cells in human body are active and mobile so that it can promote metabolism and blood circulation. Consequently, far-infrared radiation is "propagated" in the human body by riding on water molecules that circulate in the body systems, as water constructs over 70% of human body and while the highly polymerized human body is made of protein, cells, nucleic acid, enzymes, and so on.

Numerous clinical studies have manifested various effects of far infrared radiation on human bodies such as rising in subcutaneous temperature, enhancement of blood circulation and metabolism, mitigation of sensitive nerves, and so on. Studies also demonstrated that exposure to far infrared radiation could activate the strained molecules in stressed muscles and help recovering from fatigue.

The far infrared ray emitting body is typically composed of oxides selected from the group consisting alumina, silica, alumina hydrate, silica hydrate, zirconia, lithium oxide, magnesium oxide, calcium oxide, titanium oxide, or a mixture of said oxides.

The present inventor has undertaken extensive studies to select a far infrared rays generating composition that possesses a strong radiation capacity in the desirable band of wavelengths, namely 3 to 14 $\mu$m. Strong far infrared radiation is required to establish an irradiation zone so that it may activate the shower water even without directly contacting the running water. Consequently, the inventor found that the far infrared ray generating composition fabricated by the method involving inorganic powders having particle sizes smaller than 3,000 angstroms provided a larger radiation effect that could be attributed to larger specific radiation surface areas of the particles. The inventor further found that only those far infrared rays emitting body comprising mixtures of compounds having ultrafine inorganic powders with particle sizes smaller than 1,000 angstroms, preferably below 200 angstroms, would emit considerable radiation that could effectively activate the water at a rather significant level even at a distance of one inch away from the water.

Therefore, this invention relates to a water energizing device for shower bath comprising a far infrared rays emitting material made of ultrafine powders. The water running through the irradiation zone set up by the device of present invention attached to a showerhead is exposed to strong far infrared radiation emitting from the device. It absorbs and stores the photon energies of far infrared emission. As it eventually contacts the skin of human body, the energized water can either vigorously react with unhealthy chemical residuals on the skin for easy washing off or for skin and hair care, neutralize ionizing action in the strained molecules in stressed muscles and help recovering from fatigue, or release photons that permeate into the body to stimulate the tissue within and balance the activation of body function.

OBJECTS AND ADVANTAGES

Accordingly, one object of this invention is to provide a water energizing device that can charge the water within or outpouring from a showerhead and transport the photon energies of far infrared radiation to human body for enhancement of the body's function and health.

Another object of the present invention is to provide a simple and easy-to-use device that helps effectively clean up unwanted chemicals and wastes on the skin and the hair.

Another object of the present invention is to provide a simple, easy-to-use, and yet effective therapeutic device that helps the body recover from stress and fatigue.

Another object of the present invention is to provide a simple, easy-to-use, and yet effective therapeutic device that helps activate the metabolization of the head skin and encourage a hair care action.

These objectives are achieved by a shower water energizing device comprising a far infrared ray emitting material made of ultrafine powders.

Other objects, features and advantages of the present invention will hereinafter become apparent to those skilled in the art from the following description.

DRAWING FIGURES

FIG. 1 shows a schematic view illustrating one embodiment of the present invention with a far infrared rays emitting material disposed adjacent to and exterior of the showerhead.

FIG. 2 shows a schematic view illustrating another embodiment of the present invention with a far infrared rays emitting material taking a form of a ring and being attached to the showerhead.

FIG. 3 shows a schematic view illustrating another embodiment of the present invention with a far infrared rays emitting material disposed in a housing that is inserted between the water supply conduit and the showerhead.

REFERENCE NUMERALS IN DRAWINGS

11 Far infrared rays emitting material
12 Attachment means
13 Housing means
14 Showerhead
15 Water supply conduit

SUMMARY

In accordance with the present invention a water energizing device for shower bath comprises a far infrared rays emitting composition made of ultrafine powders. The device is used to activate the water running through and outpouring from the showerhead and to transport the photon energies from far infrared radiation to the skin of human body, using water as a medium, for skin care, enhancement of circulation and metabolism of the body, or other therapeutic purposes.

DETAILED DESCRIPTION OF THE INVENTION

The device of the present invention comprises a far infrared rays emitting material 11. FIG. 1 illustrates one embodiment of the present invention with a far infrared ray emitting body in a form of a bead 11 attached to the showerhead 14 with an attachment means 12. For example, a far infrared rays emitting bead 11 may have a typical diameter of about ½ to 1 inch. An attachment means can be a simple metal string shaped to hold the bead and meanwhile clamp to the showerhead or water conduit. The far infrared emitting body can also be formed by plural far infrared radiating elements in a housing, or housings. There is no need of directly contacting the water with the far infrared radiating material. The far infrared rays emitting body 11 may be placed where all outpouring water may flow through its irradiation zone within a radius about one inch.

FIG. 2 shows a schematic view illustrating another embodiment of the present invention with a far infrared rays emitting material 11 taking a form of a ring. The diameter of the far infrared rays emitting ring 11 is about 2 inches with a thickness of 3/32 inch. The ring can be attached to the showerhead by threading or clamping.

FIG. 3 shows another embodiment of the present invention with a far infrared rays emitting element or plural far infrared rays emitting elements 11 in a housing that is inserted between the water supply conduit 15 and the showerhead 14. As water begins to flow through a water supply conduit, it will exit the conduit and enter into an inlet port of the housing to course through the housing and flows around the far infrared emitting elements 11. The far infrared exposed water will proceed into the showerhead 14 and outpour form it.

EXAMPLE

A qualitative and comparative method was employed to measure the far infrared radiation strengths during selecting ceramic compositions and particle sizes. A regular for-family-use liquidized natural gas burner was used as a measurement tool. It was known that far infrared radiation could penetrate rubber hose and activate the fuel passing through in the hose. The dipole-dipole interactions between hydrocarbon molecules resulting in the formation of large clusters can be overcome by a far infrared radiation in the same wavelength band as designed in the present invention. The far infrared radiated fuel led to a more complete combustion because of smaller fuel particles that were easier to mix with oxygen uniformly. It thus resulted in a stronger flame. Accordingly, the relative radiation strengths from various ceramic compositions with different particle sizes could be evaluated and determined qualitatively based upon the quantified relative changes in the flame's strengths.

A commercially available ceramic composition that had a particle size around 200 um and a wavelength band between 3 $\mu$m to 14 $\mu$m was thus eventually chosen and used to make a bead. The diameter of the bead was approximately ¾ inch and the bead was hanged in front of the showerhead. It was reported that after one week showering with the energized water, the skin condition of a patient suffering from itching and rash had been improved.

CONCLUSION, RAMIFICATIONS, AND SCOPE

According to the present invention, a shower water energizing device comprising a far infrared rays emitting material having a particle size smaller than 3,000 angstrom, preferably 200 angstrom or smaller, can effectively activate the water running through its far infrared radiation zone and transport the photon energy from the radiation to the skin of human body, using water as a medium. As a result, this device can help improve the body's skin condition as well as recover from stress and fatigue. The device can be used to maintain the health of human body or for other therapeutic purposes.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

I claim:

1. A water energizing device for shower bath for enhancement of human health conditions, said device consisting of essentially a far infrared rays emitting material whereby the water running through the far infrared irradiation zone formed by the said far infrared rays emitting material is exposed to far infrared emission, said far infrared rays emitting material being formed of far infrared rays emitting particles having an ultrafine particle size, and a radiation capacity in the band of wavelengths between 3 and 14 microns.

2. The water energizing device in accordance with claim 1 wherein the particles are selected from the group consisting of alumina, silica, alumina hydrate, silica hydrate, zirconia, lithium oxide, magnesium oxide, calcium oxide, titanium oxide, or a mixture of said oxides.

3. The far infrared ray emitting body in accordance with claim 1 wherein said ultrafine powder has a particle size is 3,000 angstroms or below.

4. The far infrared ray emitting body in accordance with claim 1 wherein said particle size is 200 angstroms or less.

5. The water energizing device in accordance with claim 1 wherein said far infrared ray emitting material is disposed exterior and in front of a showerhead.

* * * * *